(12) United States Patent
Glenn et al.

(10) Patent No.: US 12,069,438 B2
(45) Date of Patent: Aug. 20, 2024

(54) SENSOR MOUNTING FEATURES IN A CUSTOM-FITTED HEARING DEVICE SHELL

(71) Applicant: STARKEY LABORATORIES, INC., Eden Prairie, MN (US)

(72) Inventors: Janet Glenn, Minneapolis, MN (US); Craig Feldsien, Eden Prairie, MN (US); Toto Saykeo, Eden Prairie, MN (US); Justin Barlow, Minneapolis, MN (US)

(73) Assignee: STARKEY LABORATORIES, INC., Eden Prairie, MN (US)

( * ) Notice: Subject to any disclaimer, the term of this patent is extended or adjusted under 35 U.S.C. 154(b) by 177 days.

(21) Appl. No.: 17/893,344

(22) Filed: Aug. 23, 2022

(65) Prior Publication Data

US 2023/0108893 A1   Apr. 6, 2023

Related U.S. Application Data

(60) Provisional application No. 63/251,158, filed on Oct. 1, 2021.

(51) Int. Cl.
*H04R 25/00* (2006.01)
*G01K 1/08* (2021.01)
(52) U.S. Cl.
CPC .............. *H04R 25/60* (2013.01); *G01K 1/08* (2013.01); *H04R 25/658* (2013.01)

(58) Field of Classification Search
CPC .... H04R 25/65; H04R 25/658; H04R 25/659; H04R 25/652; H04R 1/1016; H04R 1/1058
See application file for complete search history.

(56) References Cited

U.S. PATENT DOCUMENTS

| 8,885,858 | B2 | 11/2014 | Nielsen |
| 10,284,975 | B2 | 5/2019 | Higgins et al. |
| 11,375,326 | B2 | 6/2022 | Blumer et al. |
| 2019/0208304 | A1 | 7/2019 | Cohen et al. |

FOREIGN PATENT DOCUMENTS

| KR | 102316908 | 10/2021 | |
| WO | WO-2018099562 A1 * | 6/2018 | ........... H04R 25/659 |

\* cited by examiner

*Primary Examiner* — Kile O Blair
(74) *Attorney, Agent, or Firm* — Mueting Raasch Group

(57) ABSTRACT

An ear-wearable electronic device includes a shell having a uniquely-shaped outer surface that corresponds uniquely to an ear geometry of a user of the ear-wearable device. The device includes an elongated sensor assembly. A mounting bridge is formed integrally with the shell and has a mounting surface that supports the elongated sensor assembly. An elongated void is in the shell that exposes the mounting surface of the mounting bridge. The shell includes an access void that extends from the inner surface to the outer surface of the shell near a first end of the mounting bridge. The access void is larger than a minor cross section of the elongated sensor assembly such that the elongated sensor assembly is able to pass through the access void and be held against the mounting surface.

20 Claims, 11 Drawing Sheets

SENSOR MOUNTING FEATURES IN A CUSTOM-FITTED HEARING DEVICE SHELL

RELATED PATENT DOCUMENTS

This application claims the benefit of U.S. Provisional Application No. 63/251,158, filed on 1 Oct. 2021, which is incorporated herein by reference in its entirety.

SUMMARY

This application relates generally to ear-level electronic systems and devices, including hearing aids, personal amplification devices, and hearables. For example, a custom-fitted, hearing device shell includes sensor mounting features that ensure good sensor placement in a custom fitted shell. In one embodiment, an ear-wearable electronic device includes a shell having a uniquely-shaped outer surface that corresponds uniquely to an ear geometry of a user of the ear-wearable device. The device includes an elongated sensor assembly, such as a thermal sensor assembly. A mounting bridge is formed integrally with the shell and formed contiguously with an inner surface of the shell. The mounting bridge has a mounting surface that supports the elongated sensor assembly. An elongated void is in the shell that exposes the mounting surface of the mounting bridge. The shell includes an access void that extends from the inner surface to the outer surface of the shell near a first end of the mounting bridge. The access void is larger than a minor cross section of the elongated sensor assembly such that the elongated sensor assembly is able to pass through the access void and be held against the mounting surface. The mounting surface is positioned relative to the outer surface of the shell such that a side of the elongated sensor assembly is proximate to the outer surface.

In another embodiment, a method involves 3D-printing a shell of an ear-wearable device. The shell has an outer surface that corresponds uniquely to an ear geometry of a user of the ear-wearable device. A mounting bridge is formed integrally with the shell and formed contiguously with an inner surface of the shell. The mounting bridge has a mounting surface for fixably mounting an elongated sensor assembly to the shell. An elongated void in the shell exposes the mounting surface of the mounting bridge. The method further involves moving the elongated sensor assembly through an access void that extends from the inner surface to the outer surface of the shell near a first end of the mounting bridge. The elongated sensor assembly is mounted against the mounting surface. The mounting surface is positioned relative to the outer surface of the shell such that a side of the elongated sensor assembly is proximate to the outer surface of the shell.

The above summary is not intended to describe each disclosed embodiment or every implementation of the present disclosure. The figures and the detailed description below more particularly exemplify illustrative embodiments.

BRIEF DESCRIPTION OF THE DRAWINGS

The discussion below makes reference to the following figures.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
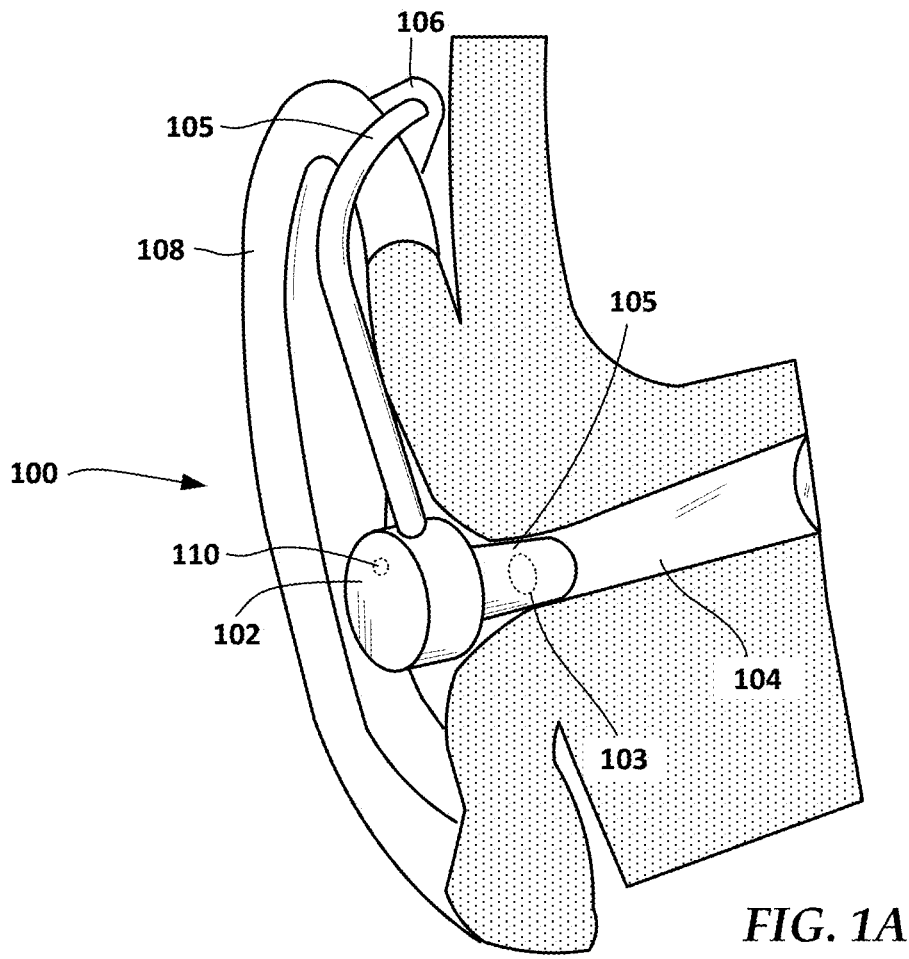
FIG. 1A is an illustration of a hearing device according to an example embodiment.

Embodiments disclosed herein are directed to an ear-worn or ear-level electronic hearing device. Such a device may include cochlear implants and bone conduction devices, without departing from the scope of this disclosure. The devices depicted in the figures are intended to demonstrate the subject matter, but not in a limited, exhaustive, or exclusive sense. Ear-worn electronic devices (also referred to herein as "hearing aids," "hearing devices," and "ear-wearable devices"), such as hearables (e.g., wearable earphones, ear monitors, and earbuds), hearing aids, hearing instruments, and hearing assistance devices, typically include an enclosure, such as a housing or shell, within which internal components are disposed.

Custom fitted hearing devices can result in ear-worn electronics with enhanced performance and comfort. A custom-fitted device may be formed, for example, by taking a mold of the user's ear and then using the mold to create a device that fits the exact contour of the user's ear. Technological developments such as three-dimensional (3D) scanning and 3D printing can increase the dimensional accuracy of custom-fitted device compared to, for example, molding of the part. Also, 3D scanning and 3D printing can increase the speed and ease with which the ear-wearable devices can be produced. This allows creating an organically shaped shell for the device that is custom fit to the individual's ear geometry to a high accuracy, e.g., within 0.1 mm.

One application of interest in ear-wearable technologies is the sensing of biometric data in the ear. Through direct contact with the surfaces of the outer ear, e.g., near the ear canal, sensors can accurately detect body temperature, pulse rate, and other metrics related to blood flow, such as blood oxygen level. This can be useful in hearing-aid devices, which are intended for long-term wear and so can unobtrusively gather health data over long-periods of time while at the same time performing its primary function of conditioning and amplifying sounds into the ear.

It has become increasingly cost-effective to perform in-ear sensing in ear-wearable devices due to the availability of low-cost yet accurate micro-sensors. An ear-wearable hearing aid will already have at least a microphone for sensing sound that is to be amplified. Other sensors may also be used in such, such as accelerometers, temperature sensors, etc., which can improve the accuracy of the sound reproduction via digital signal processing. Thus ear-wearable device architectures already include electronics (e.g., microprocessor, digital signal processors) capable of receiving and processing sensor data, and so these devices are amenable to adding biometric sensors, including biometric sensors that contact the skin within the ear.

One issue with using surface mounted sensors in the ear is that it can be difficult to position such sensors on a custom-fitted shell. If the device shell is of a standard shape, such as a tapered cylinder, it is possible to use a standard, interchangeable sensor on a whole class of devices. For example, if ten different sizes/configurations are desired, then ten different designs can be produced, in some cases automatically, e.g., using parametric computer-aided modeling. Further, it may be cost effective to use injection molding for producing those sets of shells, which is one of the cheapest methods for making a large number of devices out of plastics.

If a custom-fitted shell is desired, then the advantages of mass production manufacturing may not available. Generally, a production run for a custom fit part could just be one or two, thus traditional production methods such as injection molding would be cost prohibitive. One way of implementing a custom fit earpiece is to use a custom-fitted cover that is fitted over the end of a standard shape shell. However, such an arrangement would not be ideal for surface-mounted sensors that contact the skin, as sensors would be mounted in the shell and not the cover, and thus could not achieve direct contact. Accordingly, a system for producing individually fitted ear-wearable devices is described below, such devices utilizing ear-canal sensors that are custom placed for each ear for which it is fitted. The system allows the design and production of custom-fitted ear-wearables that utilize interchangeable sensors placed at or near a surface of the device shell for direct contact measurements. The device shells can have other features that are also customize-fitted, such as cable retention features. Such devices can be produced at scale at reasonable cost.

In FIG. 1A, a diagram illustrates an example of an ear-wearable device 100 according to an example embodiment. The ear-wearable device 100 includes an in-ear portion 102 that fits into the ear canal 104 of a user/wearer. The ear-wearable device 100 may also include an external portion 106, e.g., worn over the back of the outer ear 108. The external portion 106 is electrically coupled to the internal portion 102. The in-ear portion 102 may include an acoustic transducer 103, where it is acoustically coupled to the ear canal 104, e.g., via a cable 105. The acoustic transducer 103 may be referred to herein as a "receiver," "loudspeaker," etc., however could include a bone conduction transducer. One or both portions 102, 106 may include an external microphone, as indicated by microphone 110. The configuration shown in FIG. 1A is referred to as receiver-in-canal (RIC), in that the receiver 103 is located in or proximate the ear canal 104, while other electronics are housed in the external portion 106, all being electrically coupled by the cable 105.

Other components of hearing device 100 not shown in the figure may include a processor (e.g., a digital signal processor or DSP), memory circuitry, power management and charging circuitry, one or more communication devices (e.g., one or more radios, a near-field magnetic induction (NFMI) device), one or more antennas, buttons and/or switches, for example. The hearing device 100 can incorporate a long-range communication device, such as a Bluetooth® transceiver or other type of radio frequency (RF) transceiver.

While FIG. 1A shows one example of an ear-wearable device, often referred to as a hearing aid (HA), the term hearing device of the present disclosure may refer to a wide variety of ear-level electronic devices that can aid a person with impaired hearing. This includes devices that can produce processed sound for persons with normal hearing. Some features described herein that are implemented in a MC hearing device may also be used in other devices, such as behind-the-ear (BTE), in-the-ear (ITE), in-the-canal (ITC), invisible-in-canal (IIC), receiver-in-the-ear (RITE) or completely-in-the-canal (CIC) type hearing devices or some combination of the above. Throughout this disclosure, reference is made to a "hearing device" or "ear-wearable device," which is understood to refer to a system comprising a single left ear device, a single right ear device, or a combination of a left ear device and a right ear device.

In existing RIC designs, the in-ear portion 102 can be quite small, just housing the receiver 103 and possibly the microphone 110, while all other electronics are located in the external portion 106. Although the external portion 106 could include biometric sensors, the in-ear portion 102 is the best place to incorporate these sensors. The external portion 106 may still be needed, as it would be less than ideal to locate all the electronics and power supply in a custom, in-ear, shell. Thus, the designs described herein include an external portion 106 (also referred to as a RIC body) with a custom fitted in-ear portion (also referred to as sensor shell). The combination of the external portion 106 and a custom shell in-ear portion 102 can be used to produce a hearing device with health/biometric sensors.

Figure 1B:
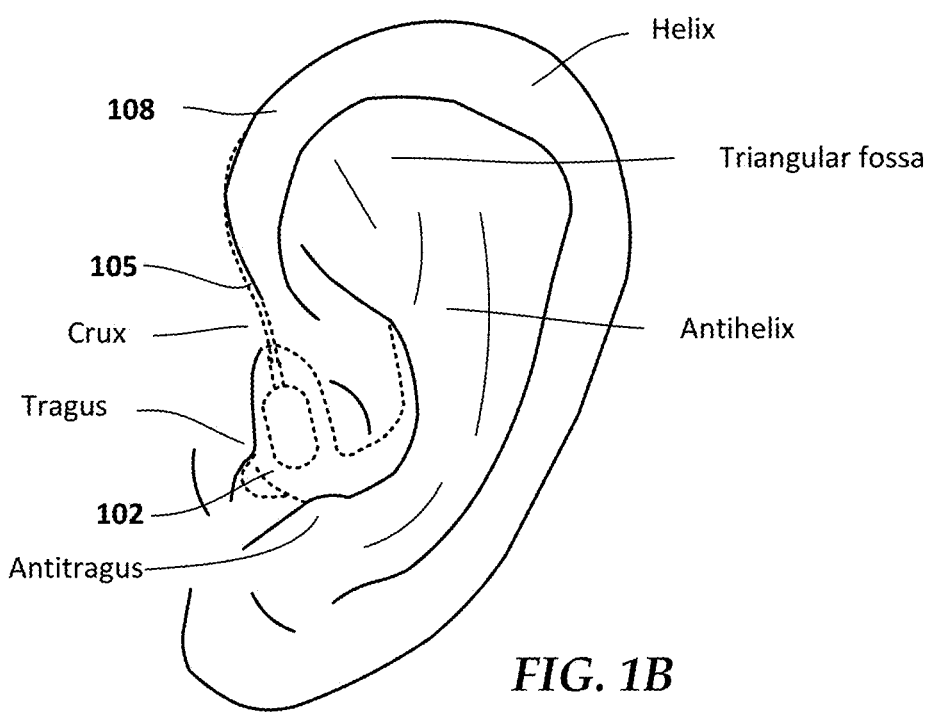
FIG. 1B is an illustration of ear geometry applicable to a hearing device.

As noted above, one challenge in making custom fitted ear-wearable devices that can be produced at scale involve integrating sensors into the complex, organically shaped outer shell that is unique for each ear. Another challenge is aligning other components with the ear, such as cables that extend from the devices. In FIG. 1B, a diagram of the outer ear 108 shows a part of the cable 105 extending along the crux of the ear (also referred to as the external auditory meatus). The location and dimensions of the crux will differ slightly for every ear, but for optimum comfort and fit, the cable 105 should be aligned with the crux within a few degrees as it exits the in-ear portion 102 (seen in FIG. 1B).

Figure 2:
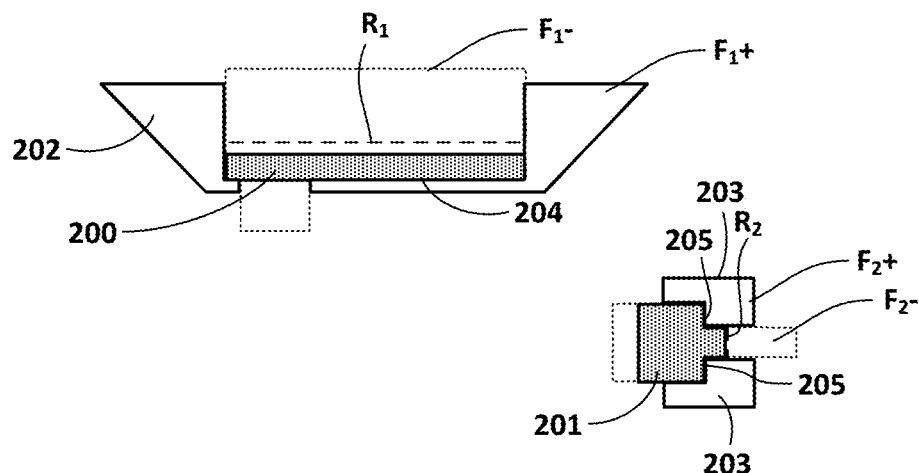
FIGS. 2-7 are two-dimensional diagrams illustrating how mounting structures are integrated with a custom-fit shell according to an example embodiment.

In FIGS. 2-7, a series of diagrams illustrate how objects such as cables and sensors with predefined and unchanging geometry can be integrated into a shell that has a different geometry for each ear in which it is used. As seen in FIG. 2, two sensors 200, 201 are shown in a simplified, two-dimensional (2D) view. For each of these sensors 200, 201, geometry of mounting structures 202, 203 is defined, e.g., in a computer aided drawing (CAD) system. The mounting structures 202, 203 are used for mounting the sensors 200, 201, although the final geometry of each mounting structure 202, 203 will differ due to the integration of the structures into a custom shell. Thus, an initial geometry of the mounting structure 202, 203 is shown in FIG. 2, this initial geometry exceeding the final dimensions of the structures when they are integrated into the shell.

The initial geometry of the structures 202, 203 includes positive features $F_{1+}$ and $F_{2+}$, a part of which are added to the shell and negative features $F_{1-}$ and $F_{2-}$, a part of which that are subtracted from the shell. The positive features $F_{1+}$ and $F_{2+}$, are drawn in solid lines and the negative features $F_{1-}$ and $F_{2-}$ are drawn in dashed lines. Note that the structures 202, 203 are initially over-defined, in that they include more positive features that will eventually be used in the final design. In other words, some of the positive features will be later removed by negative features defined by the shell geometry.

The geometry of mounting structures 202, 203 also includes reference features $R_1$, $R_2$ that are defined relative to a mounting feature of the structures 202, 203. For example, feature $R_1$ is offset from mounting plane 204 and reference feature $R_2$ is offset from mounting shoulders 205. The reference features $R_1$, $R_2$ are used to position the feature geometry relative to a corresponding feature on the shell. In this example, the reference features $R_1$, $R_2$ would be placed at or below a threshold distance from an outer feature of the shell, which ensures that the associated sensors 200, 201 are appropriately placed, e.g., close to the outer surface of the shell without extending beyond the outer surface of the shell. In order to prevent the sensors 200, 201 from extending beyond the outer surface of the shell, the reference features $R_1$, $R_2$ may be selected to ensure the sensors 200, 201 are below the outer surface of the shell even given a worst-case tolerance deviation of sensor and shell geometry. Any gaps between the outer sensor surfaces and the shell outer surface can be smoothed using a filler or coating as described below. In some other embodiments, one of the sensors 200, 201 may protrude from the shell, in which case the reference features may be selected for a target orientation such that a surface of the sensor extends out of the outer surface of the shell by a protrusion distance into the ear surface.

Figure 3:
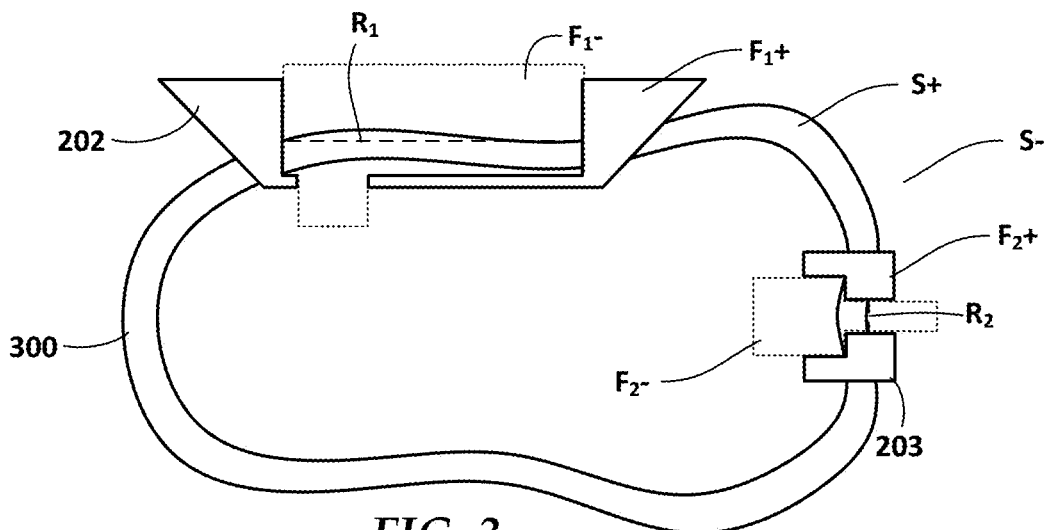
Figure 4:
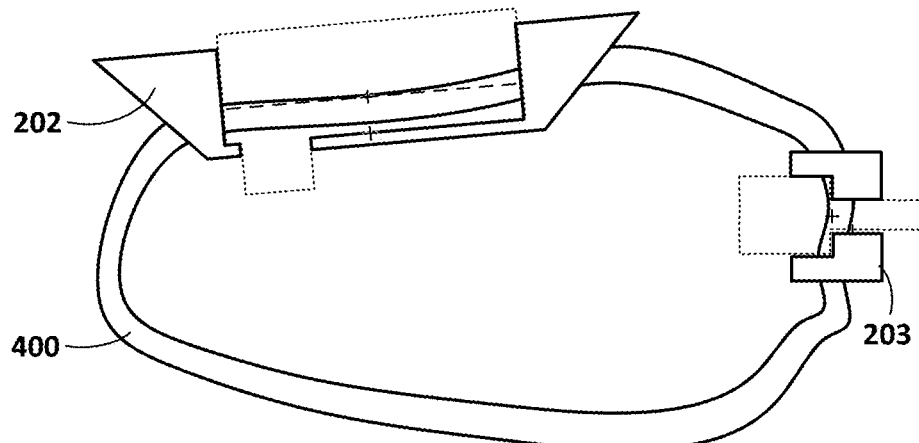

As seen in FIG. 3, a shell structure 300 is defined based on a specific ear geometry. The shell structure 300 is also represented by positive and negative features S+, S−, which generally define a thin-walled structure that encloses an inner volume. Note that the negative feature S− surrounds the outer surface of the shell structure 300, as the outer counters of the structure should remain mostly unchanged after adding mounting structures and sensors. As seen in FIG. 4, another shell 400 is similarly defined, this other shell 400 uniquely corresponding to a different ear geometry.

Figure 5:
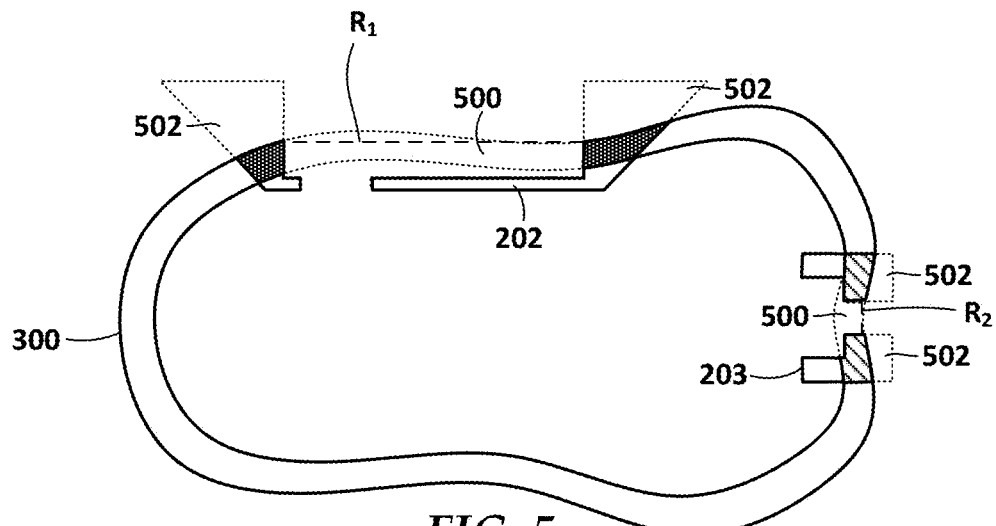

In FIG. 5, a diagram shows how a union operation affects the shell 300 and mounting structures 202, 203. For purposes of this disclosure, a union between a negative feature and a positive feature results in subtracting the negative feature from the positive feature. If a positive feature occupies the same space as another positive feature, they are merged. All positive features that do not intersect any other positive or negative features are left as is, and all positive features left over after the union are merged into a single, contiguous structure.

Figure 6:
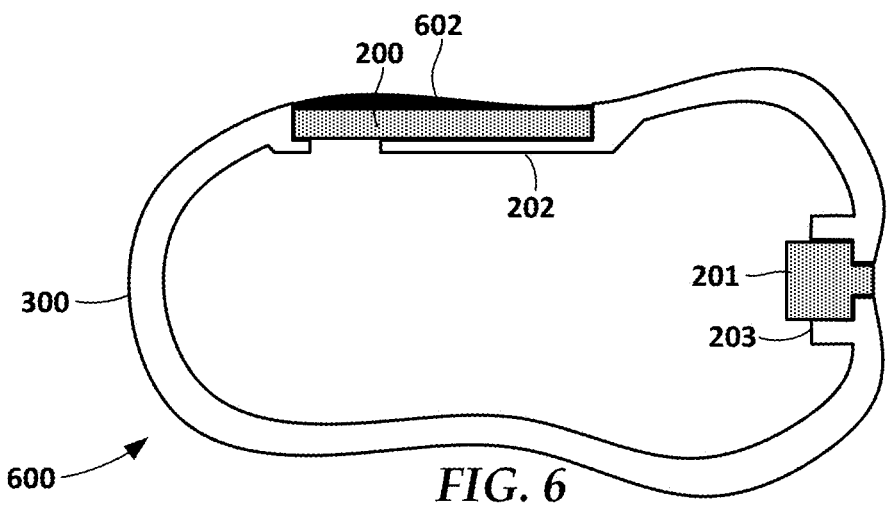
Figure 7:
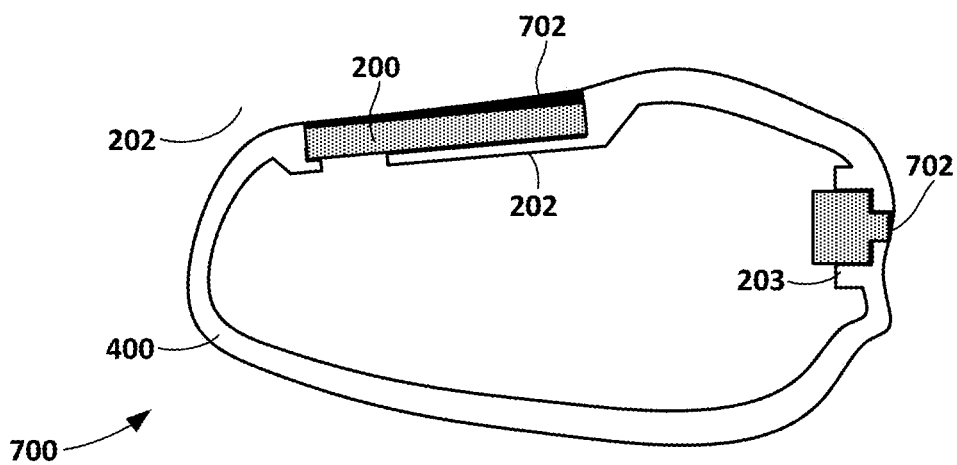

In FIG. 5, regions 500 represent parts of the original shell structure 300 that were removed by the negative features of the mounting structures 202, 203. Regions 502 represent parts of the mounting structures that were removed by the negative features of the shell structure 300. The shaded regions represent intersections between the mounting structures 202, 203 and the shell structure 300. In FIG. 6, a diagram shows the final shell 600 with the mounting structures 202, 203 integrated into the shell structure 300 as a single, contiguous structure. The sensors 200, 201 are also shown fixably mounted via the mounting structures 202, 203, and may be secured by adhesives or other fixable mounting means. Note that a final smooth contour may be formed using a coating, e.g., skim coating 602 as shown over sensor 200, and which may also be applied over sensor 201, although not shown here. In FIG. 7, a diagram shows a final shell 700 with the mounting structures 202, 203 integrated into the different, unique, shell structure 400 shown in FIG. 4. The sensors 200, 201 and skim coatings 702 are also seen fixably mounted in FIG. 7.

As noted above, an in-ear shell incorporating biometric or health sensor will typically be coupled to an external portion via a cable. Therefore, the shell will incorporate mounting features that secure the cable to the shell. Because part of the shell will be visible in the user's ear, it is desirable to improve the aesthetic of the adhesive system for the cable while maintaining the desired robustness and reliability of the hearing device. In embodiments described below, this involves a specially designed cable exoskeleton and a shell-integrated cable retention that adheres the cable to the sensor shell.

Figure 8:
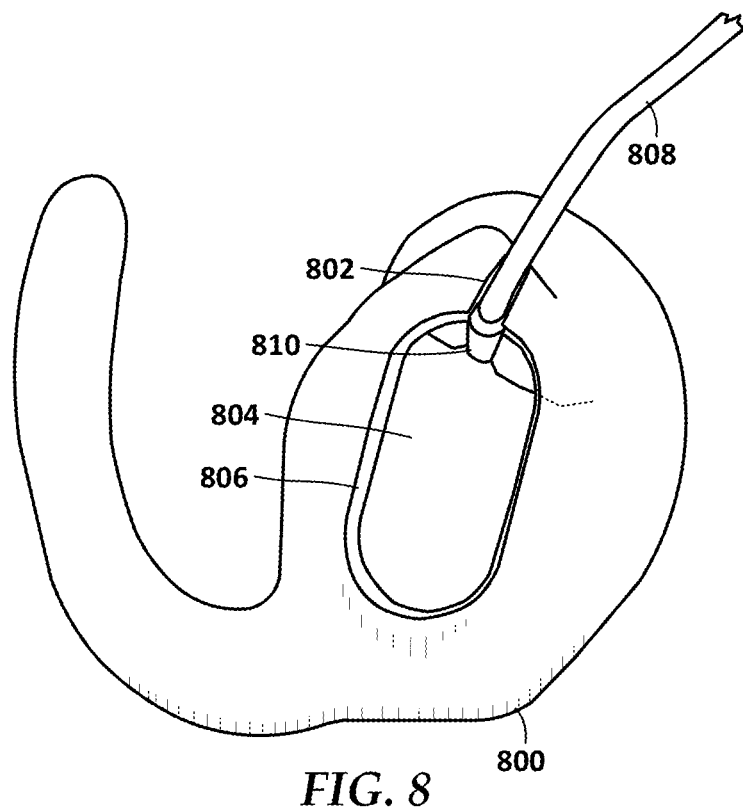
FIGS. 8 and 9 are perspective views showing faceplate and cable features according to an example embodiment.

In FIG. 8, a perspective view shows cable retention features of an ear-wearable device according to an example embodiment. The ear-wearable electronic device includes a shell 800 with a cable retention slot 802. The shell 800 also optionally includes a faceplate void 804 that has a curved and beveled perimeter edge 806. The faceplate void 804 facilitates access to one or more devices installable into the shell 800. The cable retention slot 802 intersects the beveled perimeter edge 806, such that a cable 808 coupled to internal electronics (e.g., sensors, not shown) at a distal end can be introduced into the faceplate void 804. After the internal electronics are fastened to their respective mounting structures, the cable 808 can be secured into the cable retention slot 802.

The shell 800 can be 3D printed using a liquid resin process that utilizes a resin for audiology applications, such as provided by Pro3dure® medical LLC, e.g., GR-1 resin. This resin may also be used for skim coating as described elsewhere herein. Various adhesives may be used to secure devices to the shell, such as rigid adhesives (e.g., Loctite® 4307) and silicone adhesives (e.g., Loctite® 5056). The shell 800 may be oriented during printing such that the faceplate void 804 is aligned with (e.g., facing) the build platform, with the canal tip being the last scaffolding printed. This ensures that the more critical tolerances (e.g., those that can adversely affect fit in the ear) are formed in the X-Y dimensions and not in the Z-dimension (e.g., the scaffolding tolerance), which is not as controllable due to the Z-dimension depending on the thickness of resin that is hardened by ultraviolet light for each layer. For example, Z-direction tolerance may be as high as 0.012" worst case, which is higher than the worst-case tolerances in the X-Y directions.

The cable 808 may be made of a flexible plastic material that has a low durometer, is co-extruded, and has wire bundles and Kevlar strands for support. The cable retention slot 802 is designed to cradle the co-extruded cable 808, providing both strain relief support and direction the cable 808 in a desired direction as it exits the shell 800. There is a blunt 810 at a jacket-terminating end of the cable. As will be described in further detail below, the blunt 810 may be octagonally-shaped and includes features that indicated to the building technician how to axially locate the cable 808 within the shell 800. This sets the depth of the cable 808 within the shell 800. The cable 808 has a bend that is designed to be aligned with the crux of the ear where the cable 808 connects with the shell 800.

Figure 9:
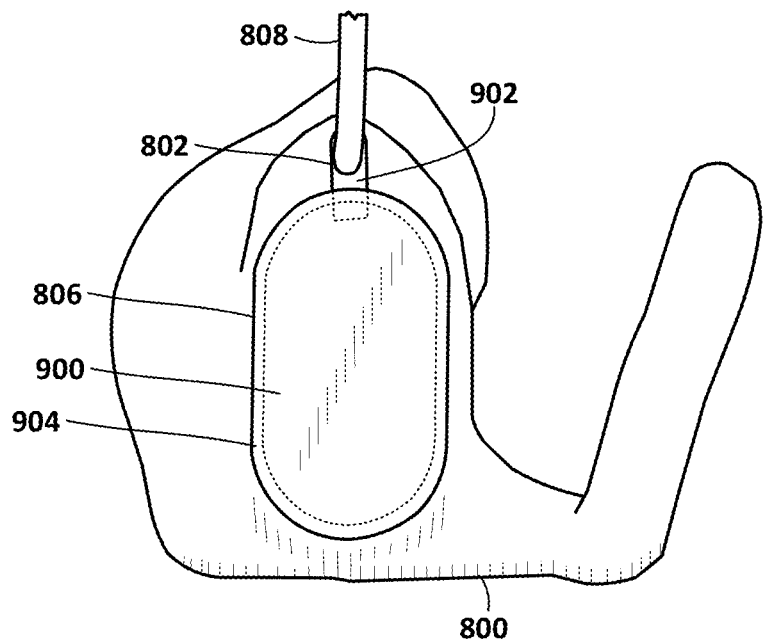

In FIG. 9, the shell 800 is shown with a faceplate 900 with a beveled edge 904 that mates with the perimeter edge 806. The faceplate 900 has an unbroken covering surface that matches the outer surface of the shell 800 surrounding the faceplate void 804 and traps the cable 808 into the cable retention slot 802. A biocompatible filler 902 (e.g., silicone or rigid adhesive) is backfilled into the cable retention slot 802 after the faceplate 900 is installed, which creates a gasket around the cable 808 at its exit point from the shell 800. The filler 902 seals off the shell 800 and acts as a strain relief. Using a material such as silicone (e.g., Loctite® 5056) for the filler 902 provides an aesthetically pleasing appearance even after the expected life-cycle of wear and tear on the ear-wearable device.

The cable 808 includes conductors that electrically couple an external controller (e.g., external portion 106 shown in FIG. 1A) with a receiver (e.g., receiver 103 shown in FIG. 1A) mounted within the shell 800. The shell 800 also includes one or more sensors that are also coupled to the controller by conductors of the cable 808. In particular, a sensor near the surface of the shell 800 is provided that is in close proximity to an ear surface enabling accurate biometric measurements to be made. As noted above, it can be challenging to accurately place such sensors in a custom-fitted shell, as well as providing for straightforward assembly of the sensor into the shell. In embodiments described below, mounting features and assembly methods are described for an elongated thermal sensor assembly.

Figure 10:
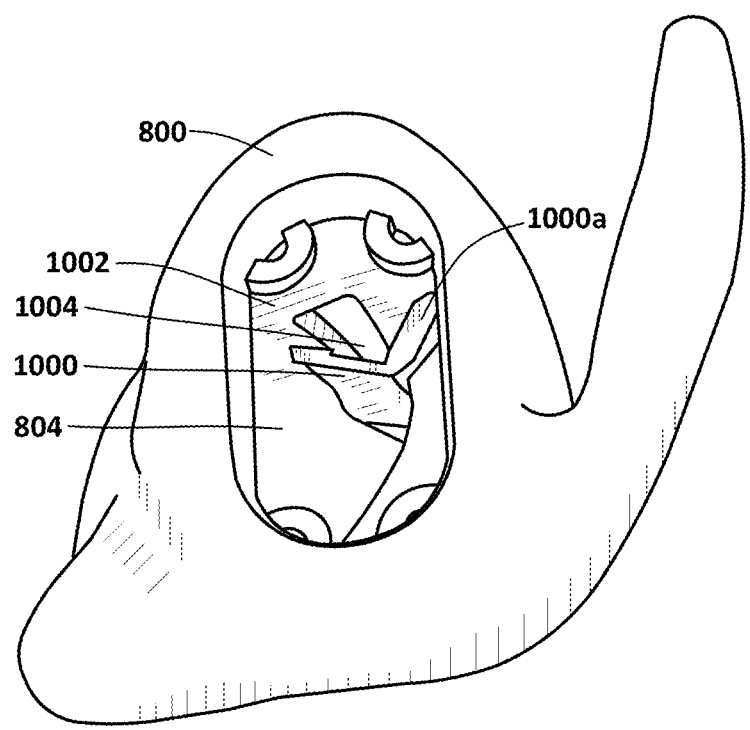
FIGS. 10, 11, and 12 are perspective views showing elongated sensor mounting features according to example embodiments.
Figure 11:
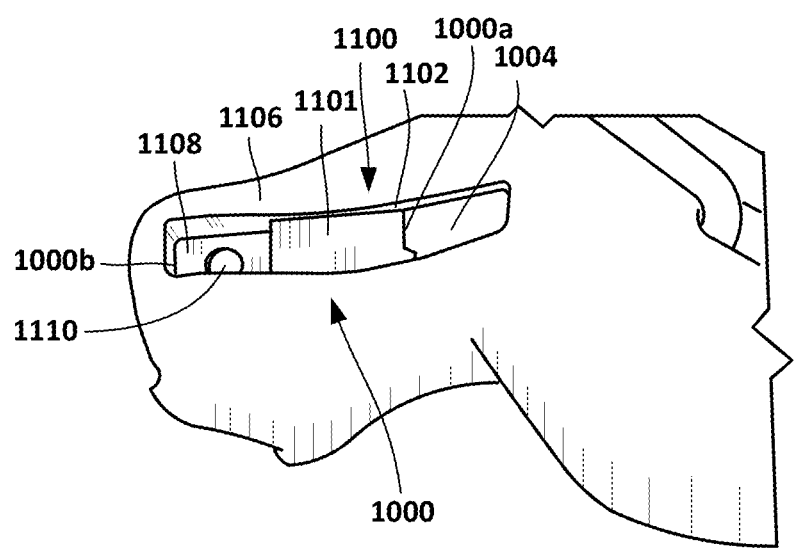
Figure 12:
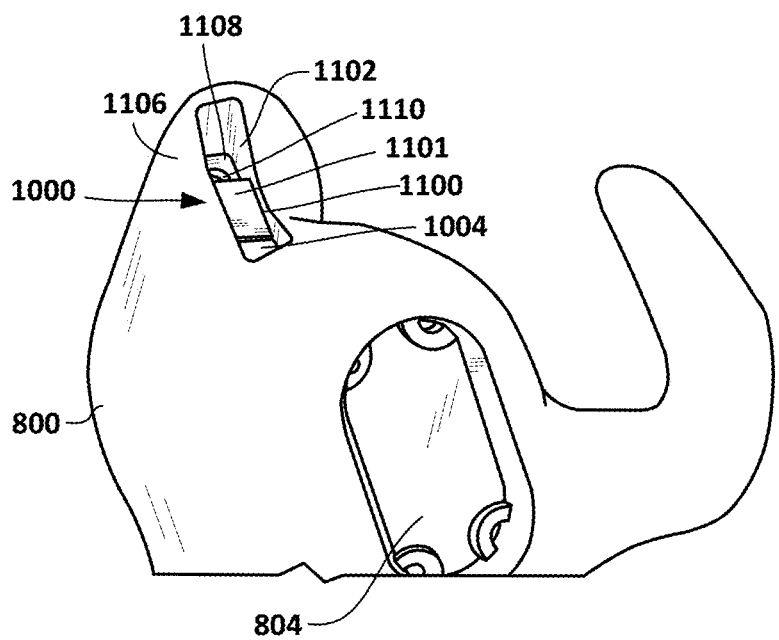

In FIGS. 10-12, perspective views of the shell 800 show details of thermal sensing mounting features according to an example embodiment. A mounting bridge 1000 is formed integrally with the shell 800 and formed contiguously with an inner surface 1002 of the shell. As best seen in FIGS. 11 and 12, the mounting bridge 1100 includes a mounting surface 1101 configured for supporting the elongated sensor assembly to the shell 800. An elongated void 1102 in the shell exposes the mounting surface 1101 of the mounting bridge 1000.

An access void 1004 extends from the inner surface 1002 to and outer surface of the shell near a first end 1000a of the mounting bridge. The access void 1004 is larger than a minor cross section of the elongated sensor assembly such that the elongated sensor is able to pass through the access void 1004 and be held against the mounting surface 1101. The mounting surface 1101 is positioned relative to the outer surface 1106 of the shell 800 such that a side of the elongated sensor assembly is proximate to the outer surface 1106.

The mounting bridge 1000 includes a thermal barrier 1108 at a second end 1000b opposite the first end 1000a. A distal end of the thermal sensor assembly is located over the thermal barrier 1108 when installed, and a sensing element at the distal end of the sensor assembly is placed within a pocket formed by the thermal barrier. The thermal barrier 1108 acts as an insulator, which helps increase the sensitivity of the thermal sensor element, e.g., by reducing heat transfer into the interior of the shell 800. The thermal barrier 1108 includes a drain hole 1110 that helps ensure material doesn't build up between the thermal barrier 1108 and the sensor. For example, the drain hole may facilitate drainage of a liquid resin into which the shell is dipped to smooth the surfaces after assembly and to skim coat the sensors.

Figure 13:
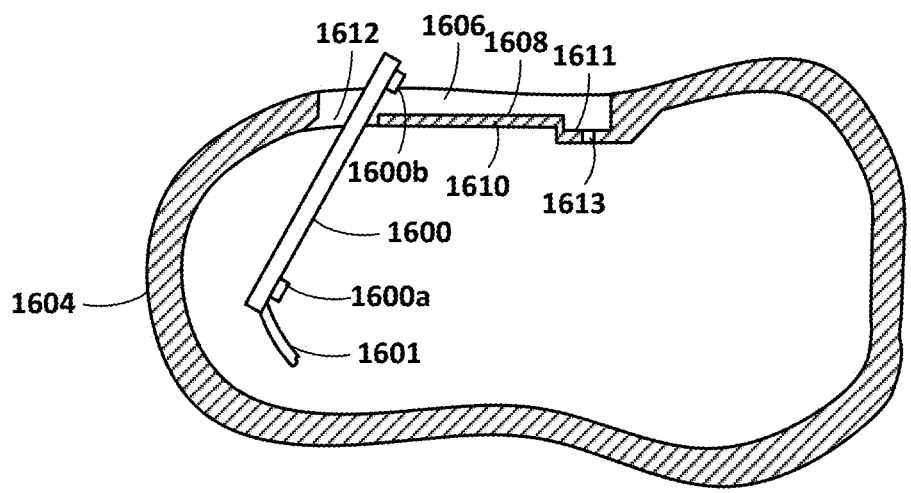
FIGS. 13, 14, and 15 are cross-sectional views showing sensor installation methods according to an example embodiment.
Figure 14:
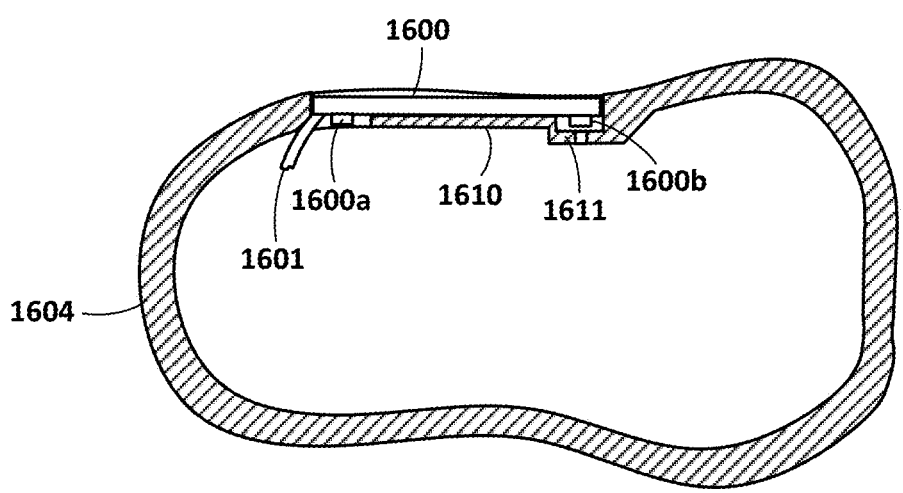
Figure 15:
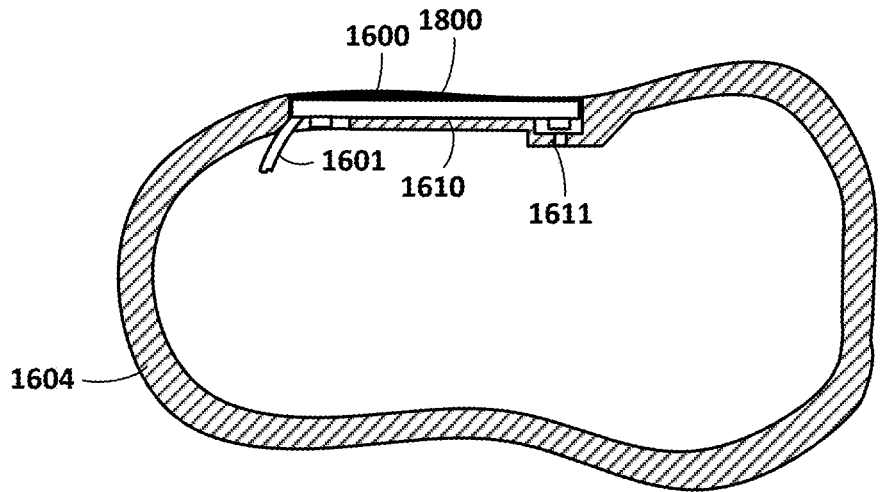

In FIGS. 13-15, a cross-sectional view shows aspects of assembling an elongated, thermal sensor assembly 1600 into a 3D-printed shell 1604 according to an example embodiment. The elongated sensor 1600 may include a flex cable, outer and inner thermal sensing elements 1600a, 1600b, solder pads, and electrical components, e.g., a capacitor. Note that more or fewer thermal sensing elements may be used. The shell 1604 includes an elongated void 1606 that exposes a mounting surface 1608 of a mounting bridge 1610. An access void 1612 extends from the inner surface to the outer surface of the shell 1604 near a first end of the mounting bridge 1610. The access void 1612 is larger than a minor cross section of the elongated sensor assembly 1600 such that the elongated sensor assembly 1600 can pass through the access void 1612 as seen in FIG. 13. Also seen in this figure is a thermal barrier 1611 at one end of the mounting bridge. A distal end of the thermal sensor assembly 1600 is located near the thermal barrier 1611 after mounting (see FIG. 14). The thermal barrier 1611 includes a drain hole 1613 that prevents material from building up between the thermal barrier 1611 and the elongated sensor assembly 1600 during and after installation. For example, post-processing of the shell 1604 may involve dipping into a liquid resin to smooth the surfaces, and the drain hole allows this liquid resin to escape.

The sensor assembly 1600 is shown attached to cable 1601, which may be strands of a larger cable that couples the illustrated in-ear portion to an external part of the hearing device. The sensor assembly 1600 is introduced through the faceplate void (e.g., faceplate void 804 in FIG. 8) where it can be attached to a mounting point within the shell 1604. As seen in FIG. 13, the elongated sensor assembly 1600 is passed through the access void 1612 and then rotated into place as seen in FIG. 14 so that a bottom surface of the sensor assembly 1600 contacts the mounting surface 1608. Note that this does not necessarily involve the elongated sensor assembly 1600 being adhered to the mounting surface 1608, although some small amount of adhesive may be used to tack the sensor assembly 1600 into place. If there is a tight fit of the elongated sensor assembly 1600 within the elongated void 1606, then friction may be sufficient to hold the sensor assembly 1600 in place for subsequent assembly. The mounting surface 1608 is positioned relative to the outer surface of the shell 1604 such that an outside-facing side of the elongated sensor assembly 1600 is proximate to the outer surface of the shell 1604, e.g., flush or slightly recessed. The sensing elements 1600a, 1600b are located within the access void 1612 and pocket formed by the thermal barrier 1611 after assembly, placing them in proximity to a surface of the wearer's ear.

As seen in FIG. 15, a final step is applying a skim coating 1800 over the exposed side of the sensor assembly 1600. The skim 1800 coating fills in gaps, permanently fastens the sensor assembly 1600, and creates a smooth outer surface near the sensor assembly 1600 that conforms to the outer surface of the shell 1604. The skim coating 1800 hermetically seals, isolates and protects the internal electronics from the environmental rigors of the ear, as well as protecting the user from internal materials and electronics.

Figure 17:
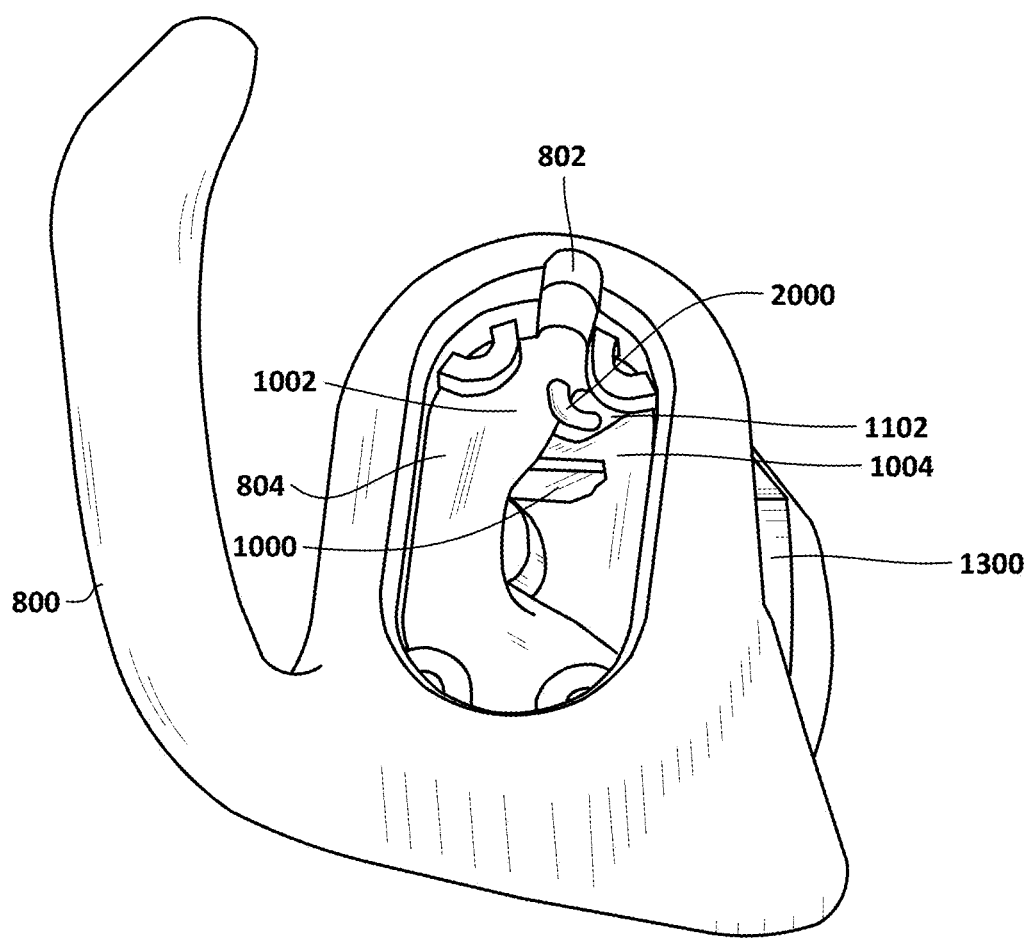
FIGS. 17 and 18 are perspective and cross-sectional views showing additional elongated sensor mounting features according to an example embodiment.
Figure 18:
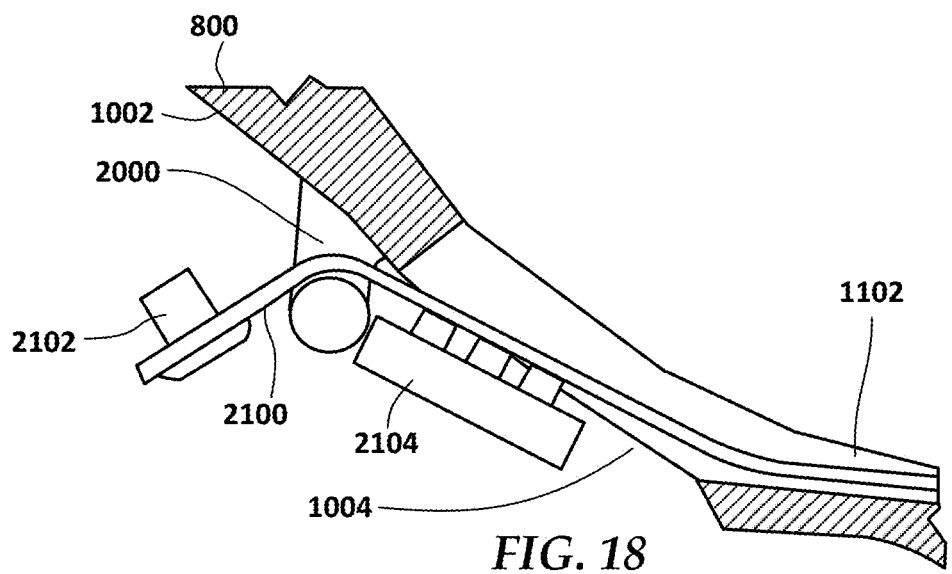
Figure 19A:
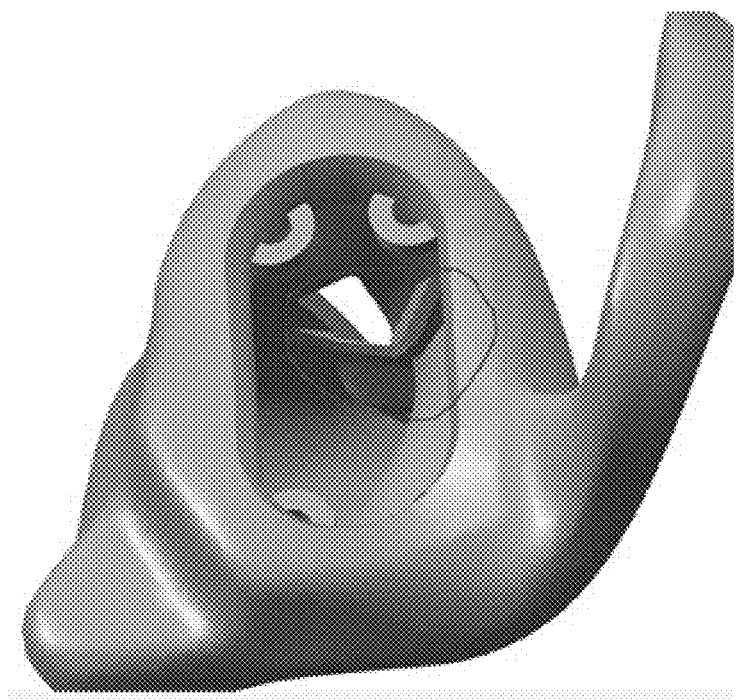
FIGS. 19*a*-19*f* are three-dimensional CAD renderings showing additional details of an ear-wearable electronic device according to example embodiments.
Figure 19B:
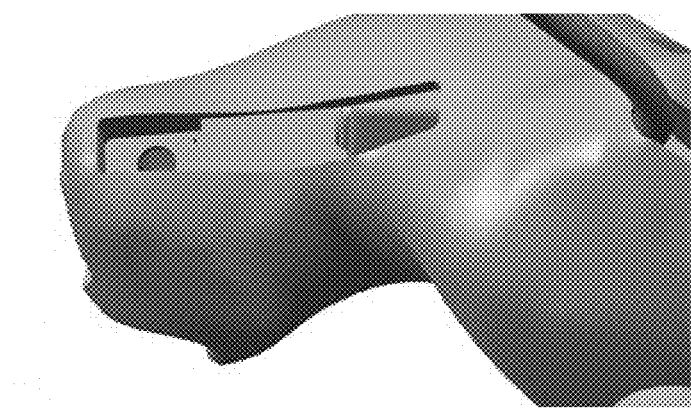
Figure 19C:
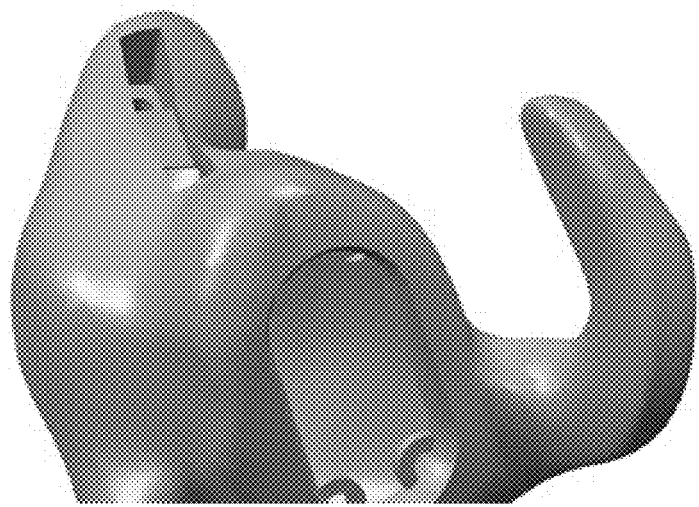
Figure 19D:
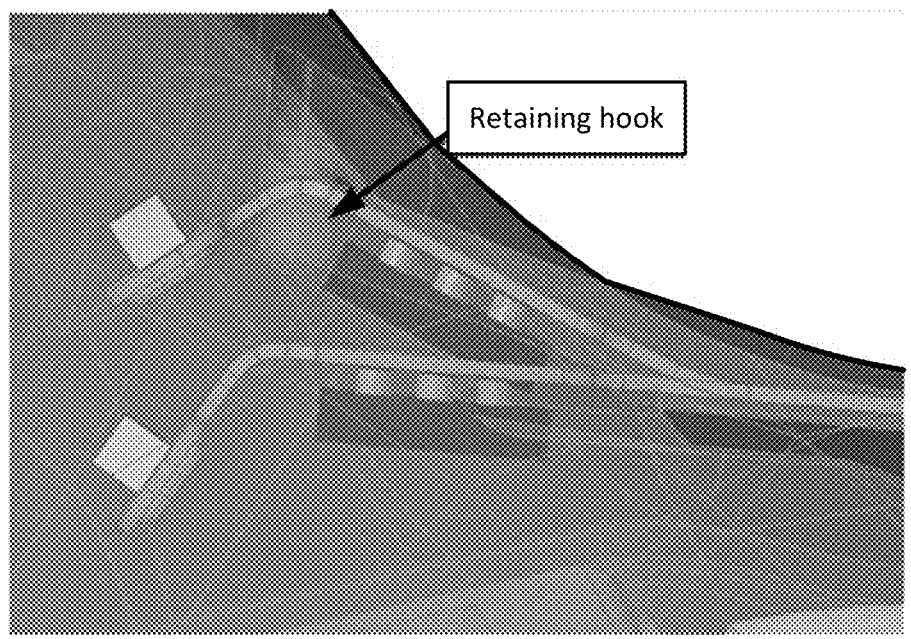
Figure 19E:
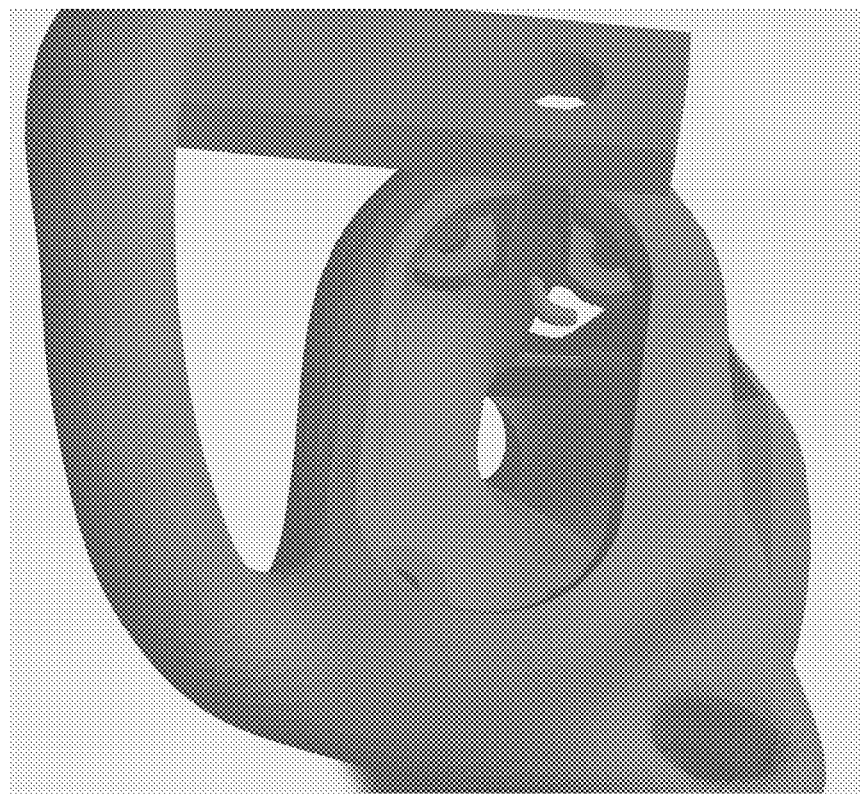
Figure 19F:
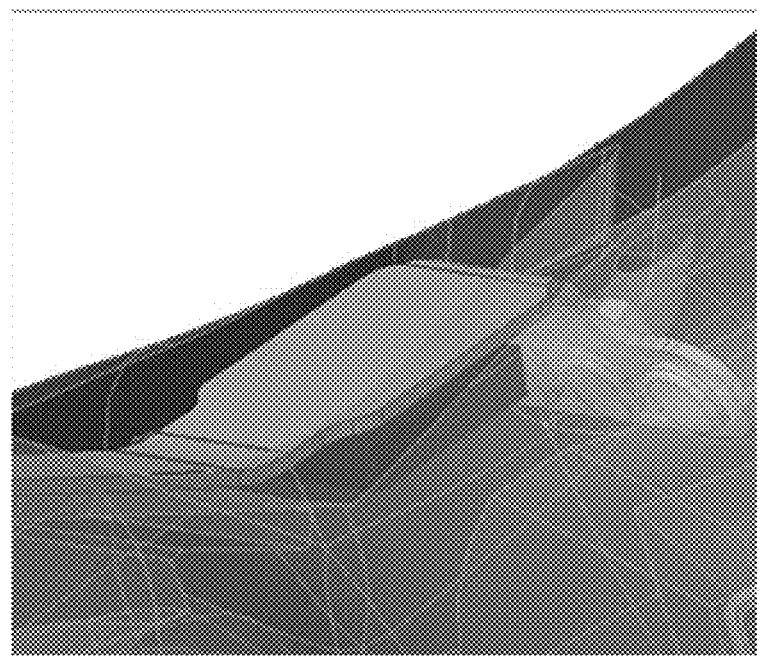

In FIGS. 17 and 18, perspective and cross-sectional views show details of a thermal sensor retaining features according to an example embodiment. In FIG. 17, the elongated void 1102 and access void 1004 can be seen through the faceplate void 804. A retaining hook 2000 can be seen mounted to the inner surface 1002 of the shell 800 near the access void 1004. As seen in FIG. 18, the retaining hook 2000 supports a flex circuit 2100 between the outer sensor 2104 and a capacitor 2102 at a terminal end of the flex circuit 2100. The retaining hook 2000 helps ensure the correct position of the outer thermal sensor 2104, and can act as a support for the flex circuit, e.g., between the capacitor 2102 and the outer sensor 2104 soldered to the flex circuit.

The retaining hook 2000 extends partially into the access void 1004. The technician can first thread the thermal sensor through the access void 1004 and the slip the flex circuit over the retaining hook 2000 during final positioning. The retaining hook 2000 can be included together with the mounting bridge 1000 and associated features when unioning the CAD models together as shown in FIGS. 2-7. Because the retaining hook 2000 will have a fixed offset between the mounting bridge 1000, the elongated void 1102, and the access void 1004, ensuring accurate placement of the thermal sensor for each unique shell geometer. This can guide longitudinal positioning of the thermal sensor, e.g., along its long axis, within the elongated void. The relative locations of the solder pad 2102 and an electrical component 2104 can assist in this positioning, as they can be separated by a distance such that the retaining hook 2000 fits between these two components.

Figure 16:
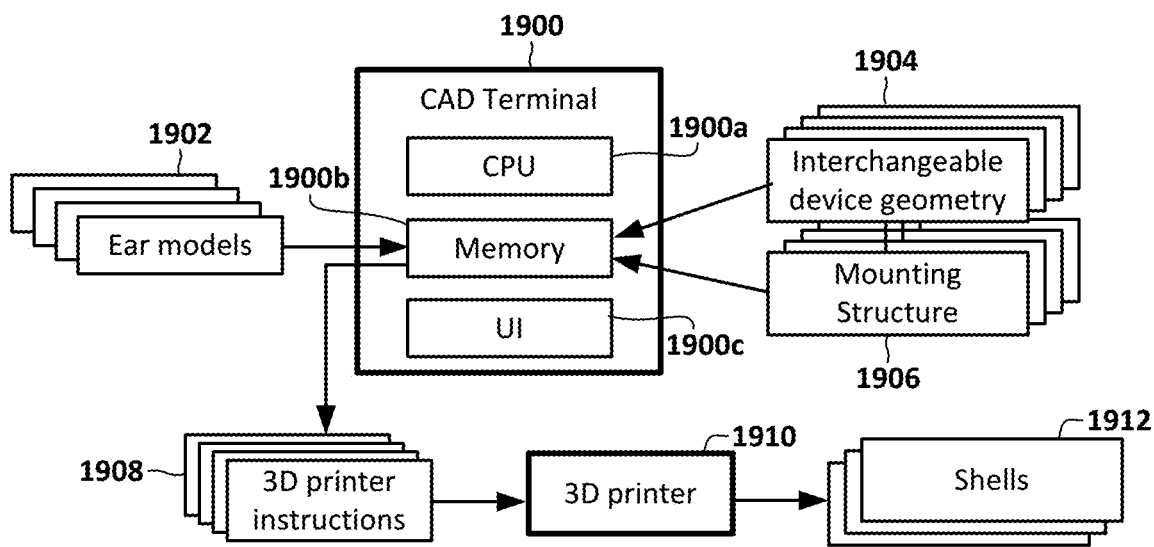
FIG. 16 is a block diagram of a system according to an example embodiment.

In FIG. 16, a block diagram shows a system according to an example embodiment. The system includes a CAD terminal 1900, which can be used to generate geometry of custom fitted shells, e.g., with biometric integrated sensors. The terminal 1900 includes one or more processors, as represented by central processing unit (CPU) 1900a. Memory 1900b is coupled to the CPU 1900a and may include volatile and non-volatile memory. The CPU 1900a is coupled to input-output lines, one of which is represented by user interface 1900c, which may include user input devices (e.g., keyboard, mouse) and output devices (e.g., monitor, virtual reality headset).

The CAD terminal 1900 is accessible by a technician and operable to receive two or more data files 1902 that describing the geometries of the two or more different ears. For example, the geometry can be scanned using a 3D scanner, and saved in a data format compatible with a CAD program running on the CAD terminal 1900. The CAD terminal 1900 may also locally or remotely store one or more geometric models 1904 of an interchangeable device, such as cable, biometric sensor, faceplate, etc. Each device model 1904 is associated with a mounting structure model 1906 that defines a maximum extent of the mounting structure, and can be used to merge with a different geometry models of a device shell that have uniquely-shaped outer surfaces that correspond a geometry of different ears.

The CAD terminal 1900 runs software that can generate a shell model based on the geometry of the ear. The shell model defines at least part of the organically-shaped outer surface of a shell. Via the user interface 1900c, the technician can identify a target feature of the geometry of the respective ear on the shell model. The user interface 1900c also facilitates locating the reference feature of the mounting structure relative to the target feature such that the interchangeable device will be located at the target orientation relative to the outer surface of the shell. The CAD terminal 1900 can then merge the shell model with the geometric model of the mounting structure to obtain a final configuration of the shell and the mounting structure.

The final configuration of the shells is used to produce the instructions 1908 for a 3D printer 1910. Each set of the instructions 1908 produces a uniquely shaped shell that is able to fit any of the interchangeable devices defined by geometry models 1904 such that the interchangeable device is located at a target orientation relative to the outer surface of the shell. The 3D printer 1910 then prints the shells 1912, which can then be used to build a hearing device as described herein.

In FIGS. 19a-19f, three-dimensional CAD renderings show additional details of an ear-wearable electronic device according to example embodiments. This document discloses numerous example embodiments, including but not limited to the following:

Example 1 is an ear-wearable electronic device comprising: a shell having a uniquely-shaped outer surface that corresponds uniquely to an ear geometry of a user of the ear-wearable device; an elongated sensor assembly; a mounting bridge that is formed integrally with the shell and formed contiguously with an inner surface of the shell, the mounting bridge comprising a mounting surface that supports the elongated sensor assembly; an elongated void in the shell that exposes the mounting surface of the mounting bridge; and an access void that extends from the inner surface to the outer surface of the shell near a first end of the mounting bridge. The access void is larger than a minor cross section of the elongated sensor assembly such that the elongated sensor assembly is able to pass through the access void and be held against the mounting surface. The mounting surface is positioned relative to the outer surface of the shell such that a side of the elongated sensor assembly is proximate to the outer surface.

Example 2 includes the ear-wearable device of example 1, wherein the mounting surface is positioned relative to the outer surface of the shell such that the side of the elongated sensor assembly does not protrude from the outer surface of the shell. Example 3 includes the ear-wearable device of examples 1 or 2, further comprising a skim coating over the side of the elongated sensor assembly that partially fills the elongated void and conforms to the outer surface of the shell, the skim coating adhering the elongated sensor to the shell.

Example 4 includes the ear-wearable device of examples 1, 2, or 3, wherein the elongated sensor assembly comprises a thermal sensor assembly. Example 5 includes the ear-wearable device of example 4, wherein the thermal sensor assembly comprises: an outer sensing element near a cable electrically coupled to the thermal sensor assembly; and an inner sensing element located at a distal end of the thermal sensor assembly opposed to the cable.

Example 6 includes the ear-wearable device of example 4 or 5, wherein the mounting bridge comprises a thermal barrier at a second end opposite the first end, a distal end of the thermal sensor assembly being located near the thermal barrier such that a thermal sensing element is located within a pocket formed by the thermal barrier. Example 7 includes the ear-wearable device of example 6, wherein the thermal barrier comprises a drain hole that prevents material build up between the thermal barrier and the thermal sensing element.

Example 8 includes the ear-wearable device of any one of examples 1-7, wherein a region of the shell proximate the mounting bridge deviates from the ear geometry to cause an interference fit between the outer surface of the shell near the elongated sensor assembly and a surface of the user's ear. Example 9 includes the ear-wearable device of example 8, wherein the surface of the user's ear includes at least one of a tragus, an antitragus, and an ear canal.

Example 10 includes the ear-wearable device of any one of examples 1-9, wherein the shell and the mounting bridge comprise an integrally 3D printed structure. Example 11 includes the ear-wearable device of any one of examples 1-10, further comprising a retention hook that extends from the inner surface proximate the access void, the retention hook supporting a flex circuit at one end of the elongated sensor assembly and providing longitudinal positioning of the elongated sensor assembly in the elongated void.

Example 12 is a method, comprising: 3D-printing a shell of an ear-wearable device, the shell comprising: an outer surface that corresponds uniquely to an ear geometry of a user of the ear-wearable device; a mounting bridge that is formed integrally with the shell and formed contiguously with an inner surface of the shell, the mounting bridge comprising a mounting surface for fixably mounting an elongated sensor assembly to the shell; and an elongated void in the shell that exposes the mounting surface of the mounting bridge. The method further comprises: moving the elongated sensor assembly through an access void that extends from the inner surface to the outer surface of the shell near a first end of the mounting bridge; and mounting the elongated sensor assembly against the mounting surface, wherein the mounting surface is positioned relative to the outer surface of the shell such that a side of the elongated sensor assembly is proximate to the outer surface of the shell.

Example 13 includes the method of example 12, further comprising applying a skim coating over the side of the elongated sensor assembly that partially fills the elongated void and conforms to the outer surface of the shell. Example 14 includes the method of examples 12 or 13, wherein the elongated sensor assembly comprises a thermal sensor assembly. Example 15 includes the method of examples 12, 13, or 14, further comprising, after moving the elongated sensor assembly through the access void, placing a flex circuit attached to one end of the elongated sensor assembly to a retention hook that extends from the inner surface proximate the access void, the retention hook providing longitudinal positioning of the elongated sensor assembly in the elongated void.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

The invention claimed is:

1. An ear-wearable electronic device comprising:
   a shell having a uniquely-shaped outer surface that corresponds uniquely to an ear geometry of a user of the ear-wearable device;
   an elongated sensor assembly;
   a mounting bridge that is formed integrally with the shell and formed contiguously with an inner surface of the shell, the mounting bridge comprising a mounting surface that supports the elongated sensor assembly;
   an elongated void in the shell that exposes the mounting surface of the mounting bridge; and
   an access void that extends from the inner surface to the outer surface of the shell near a first end of the mounting bridge, the access void being larger than a minor cross section of the elongated sensor assembly such that the elongated sensor assembly is able to pass through the access void and be held against the mounting surface, wherein the mounting surface is positioned relative to the outer surface of the shell such that a side of the elongated sensor assembly is proximate to the outer surface.

2. The ear-wearable device of claim 1, wherein the mounting surface is positioned relative to the outer surface of the shell such that the side of the elongated sensor assembly does not protrude from the outer surface of the shell.

3. The ear-wearable device of claim 1, further comprising a skim coating over the side of the elongated sensor assembly that partially fills the elongated void and conforms to the outer surface of the shell, the skim coating adhering the elongated sensor to the shell.

4. The ear-wearable device of claim 1, wherein the elongated sensor assembly comprises a thermal sensor assembly.

5. The ear-wearable device of claim 4, wherein the thermal sensor assembly comprises:
   an outer sensing element near a cable electrically coupled to the thermal sensor assembly; and
   an inner sensing element located at a distal end of the thermal sensor assembly opposed to the cable.

6. The ear-wearable device of claim 4, wherein the mounting bridge comprises a thermal barrier at a second end opposite the first end, a distal end of the thermal sensor assembly being located near the thermal barrier such that a thermal sensing element is located within a pocket formed by the thermal barrier.

7. The ear-wearable device of claim 6, wherein the thermal barrier comprises a drain hole that prevents material build up between the thermal barrier and the thermal sensing element.

8. The ear-wearable device of claim 1, wherein a region of the shell proximate the mounting bridge deviates from the ear geometry to cause an interference fit between the outer surface of the shell near the elongated sensor assembly and a surface of the user's ear.

9. The ear-wearable device of claim 8, wherein the surface of the user's ear includes at least one of a tragus, an antitragus, and an ear canal.

10. The ear-wearable device of claim 1, wherein the shell and the mounting bridge comprise an integrally 3D printed structure.

11. The ear-wearable device of claim 1, further comprising a retention hook that extends from the inner surface proximate the access void, the retention hook supporting a flex circuit at one end of the elongated sensor assembly and providing longitudinal positioning of the elongated sensor assembly in the elongated void.

12. An ear-wearable electronic device comprising:
    a shell having a uniquely-shaped outer surface that corresponds uniquely to an ear geometry of a user of the ear-wearable device;
    a thermal sensor assembly;
    a mounting bridge that is formed integrally with the shell and formed contiguously with an inner surface of the shell, the mounting bridge comprising a mounting surface that supports the thermal sensor assembly;
    an elongated void in the shell that exposes the mounting surface of the mounting bridge; and
    an access void that extends from the inner surface to the outer surface of the shell near a first end of the mounting bridge, the access void being larger than a minor cross section of the thermal sensor assembly such that the thermal sensor assembly is able to pass through the access void and be held against the mounting surface, wherein the mounting surface is positioned relative to the outer surface of the shell such that a side of the thermal sensor assembly is proximate to the outer surface.

13. The ear-wearable device of claim 12, wherein the thermal sensor assembly comprises:
    an outer sensing element near a cable electrically coupled to the thermal sensor assembly; and
    an inner sensing element located at a distal end of the thermal sensor assembly opposed to the cable.

14. The ear-wearable device of claim 12, wherein the mounting bridge comprises a thermal barrier at a second end opposite the first end, a distal end of the thermal sensor assembly being located near the thermal barrier such that a thermal sensing element is located within a pocket formed by the thermal barrier.

15. The ear-wearable device of claim 14, wherein the thermal barrier comprises a drain hole that prevents material build up between the thermal barrier and the thermal sensing element.

16. The ear-wearable device of claim 12, wherein a region of the shell proximate the mounting bridge deviates from the ear geometry to cause an interference fit between the outer surface of the shell near the elongated sensor assembly and a surface of the user's ear.

17. A method, comprising:
    3D-printing a shell of an ear-wearable device, the shell comprising:
       an outer surface that corresponds uniquely to an ear geometry of a user of the ear-wearable device;
       a mounting bridge that is formed integrally with the shell and formed contiguously with an inner surface of the shell, the mounting bridge comprising a mounting surface for fixably mounting an elongated sensor assembly to the shell; and
       an elongated void in the shell that exposes the mounting surface of the mounting bridge;
    moving the elongated sensor assembly through an access void that extends from the inner surface to the outer surface of the shell near a first end of the mounting bridge; and
    mounting the elongated sensor assembly against the mounting surface, wherein the mounting surface is positioned relative to the outer surface of the shell such that a side of the elongated sensor assembly is proximate to the outer surface of the shell.

18. The method of claim 17, further comprising applying a skim coating over the side of the elongated sensor assembly that partially fills the elongated void and conforms to the outer surface of the shell.

19. The method of claim 17, wherein the elongated sensor assembly comprises a thermal sensor assembly.

20. The method of claim 17, further comprising, after moving the elongated sensor assembly through the access void, placing a flex circuit attached to one end of the elongated sensor assembly to a retention hook that extends from the inner surface proximate the access void, the retention hook providing longitudinal positioning of the elongated sensor assembly in the elongated void.

* * * * *